(12) United States Patent
Doherty

(10) Patent No.: US 11,478,376 B2
(45) Date of Patent: Oct. 25, 2022

(54) COMFORTABLE UNDERGARMENT DISPOSABLE DRAIN LIFT

(71) Applicant: Natalie Davis Doherty, Ocean Isle Beach, NC (US)

(72) Inventor: Natalie Davis Doherty, Ocean Isle Beach, NC (US)

( * ) Notice: Subject to any disclaimer, the term of this patent is extended or adjusted under 35 U.S.C. 154(b) by 199 days.

(21) Appl. No.: 16/272,410

(22) Filed: Feb. 11, 2019

(65) Prior Publication Data

US 2019/0247221 A1    Aug. 15, 2019

Related U.S. Application Data

(60) Provisional application No. 62/629,170, filed on Feb. 12, 2018.

(51) Int. Cl.
| | |
|---|---|
| *A61M 1/00* | (2006.01) |
| *A61F 5/44* | (2006.01) |
| *A61M 27/00* | (2006.01) |
| *A61M 25/02* | (2006.01) |
| *A41D 1/00* | (2018.01) |
| *A61M 5/32* | (2006.01) |
| *A61M 5/178* | (2006.01) |
| *A61M 39/00* | (2006.01) |
| *A61M 39/10* | (2006.01) |

(52) U.S. Cl.
CPC .............. *A61F 5/4408* (2013.01); *A41D 1/00* (2013.01); *A61M 25/02* (2013.01); *A61M 27/00* (2013.01); *A61M 1/69* (2021.05); *A61M 1/70* (2021.05); *A61M 2025/0206* (2013.01); *A61M 2209/088* (2013.01); *A61M 2240/00* (2013.01)

(58) Field of Classification Search
CPC .......... A61M 1/00; A61M 5/32; A61M 5/178; A61M 39/00; A61M 39/10; A61M 2025/0206; A61M 2209/088; A61M 2240/00; A61F 5/44
See application file for complete search history.

(56) References Cited

U.S. PATENT DOCUMENTS

| | | | | |
|---|---|---|---|---|
| 5,368,585 A | * | 11/1994 | Dokken | ............ A61F 13/15268 604/358 |
| 6,612,432 B2 | * | 9/2003 | Motson | ...................... A45F 5/00 206/305 |

(Continued)

FOREIGN PATENT DOCUMENTS

CA        2677698        *  2/2008

OTHER PUBLICATIONS

U.S. Appl. No. 87/942,739 for Pinkie and the Drains and its specimen, filed May 31, 2018 by Applicant, Mary Madigan.

(Continued)

*Primary Examiner* — Tatyana Zalukaeva
*Assistant Examiner* — Ilya Y Treyger
(74) *Attorney, Agent, or Firm* — BakerHostetler

(57) ABSTRACT

Systems and methods provide for holding surgical drain evacuators in inelastic expandable pouches. Particularly, apparatuses and methods include or utilize garments for supporting and protecting surgical drain evacuators and surgical drains include straps or belts for attaching the garment to a patient. The garments include one or more expandable pouches configured to receive a surgical drain evacuator, wherein the expandable pouch is formed of a flexible inelastic material.

19 Claims, 12 Drawing Sheets

(56) References Cited

U.S. PATENT DOCUMENTS

| | | | | |
|---|---|---|---|---|
| 8,225,973 | B1* | 7/2012 | Beilinson | A45F 3/02 |
| | | | | 224/602 |
| 9,622,920 | B2* | 4/2017 | Ashton | A61F 13/55115 |
| 2005/0049661 | A1* | 3/2005 | Koffroth | A61F 7/10 |
| | | | | 607/108 |
| 2009/0095783 | A1* | 4/2009 | Price | A45F 3/00 |
| | | | | 224/576 |
| 2011/0230863 | A1* | 9/2011 | Lentini | A61M 25/02 |
| | | | | 604/541 |
| 2013/0296814 | A1* | 11/2013 | Antholz | A61M 25/02 |
| | | | | 604/319 |

OTHER PUBLICATIONS https://www.pink-pockets.com, printed Feb. 11, 2019.
Doherty, Natalie Davis, Aug. 2015, First Prototype, Ocean Isle Beach, NC.

\* cited by examiner

COMFORTABLE UNDERGARMENT DISPOSABLE DRAIN LIFT

CROSS REFERENCE TO RELATED APPLICATIONS

This patent application claims priority to and the benefit of provisional patent application 62/629,170 filed Feb. 12, 2018, which is incorporated herein by reference in its entirety.

TECHNICAL FIELD

The disclosure concerns post-surgical and other medical care, and more particularly relates to apparatuses and techniques for managing drains and fluid receptacle for receiving drainage from a body.

BACKGROUND

There are a variety of medical circumstances which require the wear of a drain or drain pouch. One example is a mastectomy drain, which collects draining fluid from an incision site to prevent painful buildups, such as seromas, that can delay healing or become infected. Other examples include drains used for postoperative care following head or neck surgery, draining ears following a myringotomy, and others. Further, there are a variety of instances beyond surgical drains, such as catheters, where tubes or drains within the human body remove material to a receptacle outside the human body.

Many of the solutions for supporting drains or attached pouches are uncomfortable, unsanitary, unsafe, and embarrassing. There is a need for sanitary, comfortable, and discreet products for handling surgical drains, drain pouches, and similar medical apparatuses.

SUMMARY

In an embodiment of a garment or apparatus disclosed herein, a garment comprises a base panel having a first panel side, a second panel side, an inward face, and an outward face. The garment also comprises an expandable pouch attached to the outward face of the base panel and configured to receive a surgical drain evacuator, wherein the expandable pouch is formed of a flexible inelastic material. The garment also comprises a flexible closure of the expandable pouch configured to substantially occlude an opening of the expandable pouch when closed, wherein the flexible closure permits fluid communication between the surgical drain evacuator and a surgical drain disposed at least in part outside the expandable pouch. The garment also comprises an adjustable waist belt fixedly attached to the first panel side using a first belt end and configured to removably attach to the second panel side using a second belt end.

In another embodiment of an apparatus or garment disclosed herein, a garment comprises an expandable pouch configured to receive a surgical drain evacuator, wherein the expandable pouch is formed of a flexible inelastic material. The garment further comprises a flexible closure of the expandable pouch configured to substantially occlude an opening of the expandable pouch when closed, wherein the flexible closure permits fluid communication between the surgical drain evacuator and a surgical drain disposed at least in part outside the expandable pouch. The garment further comprises a strap operatively coupled to the expandable pouch, wherein the strap is configured to attach about anatomy of a wearer to whom the surgical drain is applied.

An embodiment of a method disclosed herein comprises providing a garment. The garment includes an expandable pouch configured to receive a surgical drain evacuator, wherein the expandable pouch is formed of a flexible inelastic material. The garment also includes a flexible closure of the expandable pouch configured to substantially occlude an opening of the expandable pouch when closed, wherein the flexible closure permits fluid communication between the surgical drain evacuator and a surgical drain disposed at least in part outside the expandable pouch. The flexible garment also includes a strap operatively coupled to the expandable pouch, wherein the strap is configured to attach about anatomy of a wearer to whom the surgical drain is applied. The method also includes passing the surgical drain evacuator through the flexible closure to arrange the surgical drain evacuator in the expandable pouch, wherein the surgical drain passes through the flexible closure to a drainage site.

Additional and alternative aspects will be apparent on review of other portions of this disclosure.

BRIEF DESCRIPTION OF THE DRAWINGS

So that those having ordinary skill in the art, to which the present disclosure pertains, will more readily understand how to employ the novel system and methods of the present disclosure, certain illustrated examples thereof will be described in detail herein-below with reference to the drawings, wherein.

DETAILED DESCRIPTION OF ILLUSTRATIVE EMBODIMENTS

As used herein, various material names or types (e.g., "cloth," "elastic," "lining," "plastic," "fabric") may be used to describe a particular embodiment but need not apply to all embodiments. Thus, if a closure is described as cloth, it is understood that other suitable materials, such as flexible plastic, may be utilized alternatively or in combination without departing from the scope or spirit of the disclosure.

Materials can include absorbent materials. Absorbent materials can include fluff pulp, absorbent polymers, sodium polyacrylate, polypropylene, polyester, et cetera. Other materials used throughout the construction (whether absorbent or not) can include polypropylene, polyethylene, adhesives (which can be solvent free and non-sensitizing), elastics, polyurethane, synthetic and natural rubber(s), et cetera. In embodiments, skin protectants (e.g., petrolatum, stearyl alcohol, aloe) can be included in or on materials. In embodiments, materials can be prepared using procedures intended to enhance their sanitary, medical, or comfort utility. For example, materials used can be bleached using elemental chlorine-free bleaching. Dyes and pigments used can be selected based on non-sensitizing qualities or materials using dye or pigment may be avoided altogether. Similarly, fragrances used (if any) may be selected based on non-sensitizing qualities, or materials using fragrance may be avoided altogether. Further, material can be isolated from or checked for acids (e.g., acrylic acid) to ensure they are free of contamination.

Directions described herein can be understood to describe the orientation of apparatuses when worn. Thus, the top of a waist-belt type apparatus would be the portion disposed toward a wearer's head, and a bottom toward the feet. The sides would be directed to the wearer's sides as one travels from front to back or back to front. The depth and thickness (or flatness) is appreciated as the dimension traveling outward from the body (e.g., from a point at which an apparatus contacts the user's body, clothing, medical apparatuses, et cetera). "Vertical" directions are up and down and "horizontal" directions are from side to side.

As used herein, various terminology may be used with respect to surgical drain evacuators. Drains, tubes, lines, et cetera, may be connected to a surgical site, and transmit drainage to a drain pouch, evacuator, bulb, et cetera.

While different elements of garments or apparatuses disclosed herein are described as "sewn," it is understood that other techniques for forming or combining elements can be pursued interchangeably with respect to any element herein. Alternatives to sewing can include gluing, fusing, heat pressing, pinning, stapling, tying, clipping, et cetera, alone or in combination with forming shapes or sections through folding or other techniques.

Figure 1A:
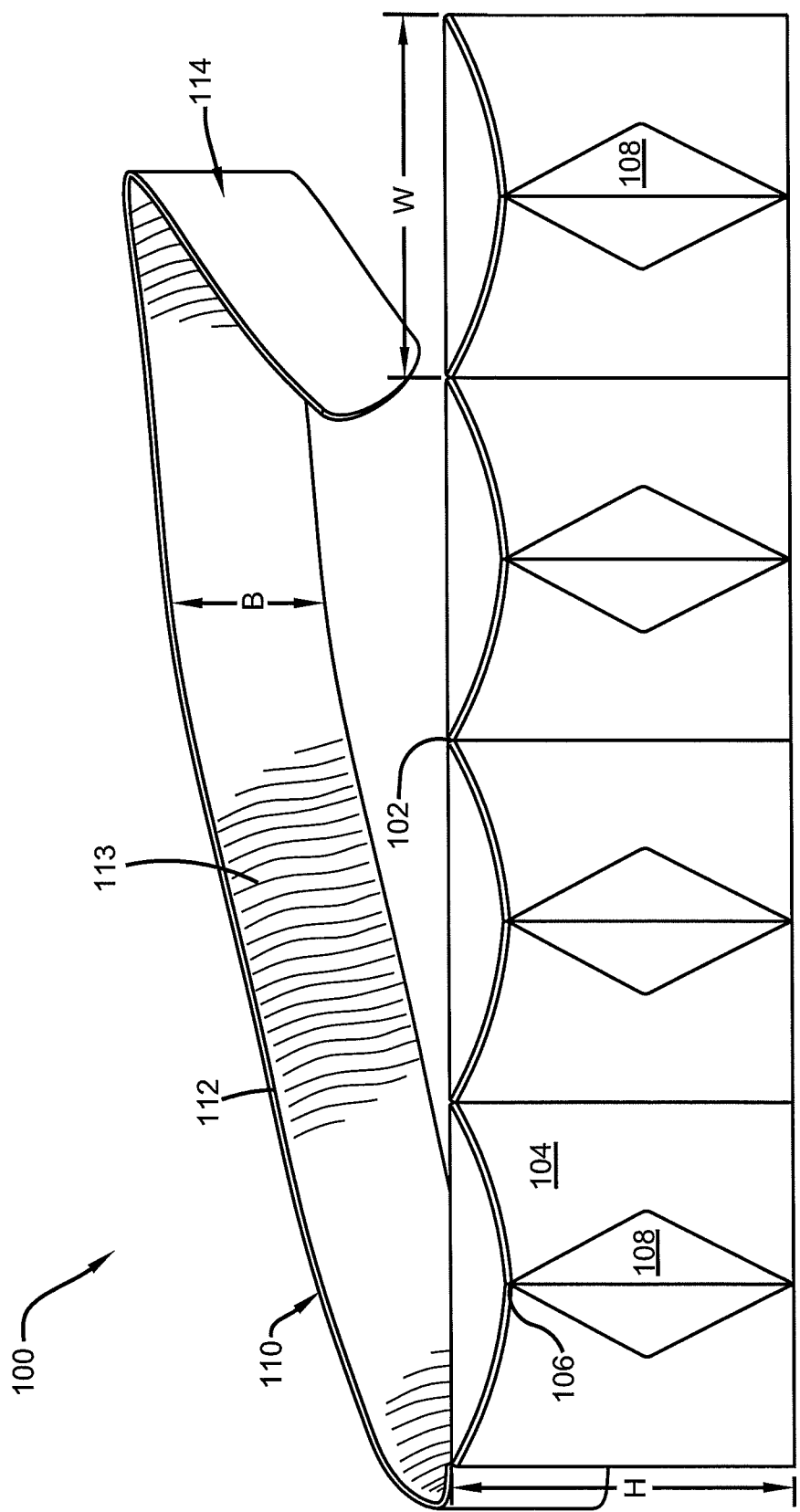
FIG. 1A illustrates an example embodiment of a drain supporting apparatus disclosed herein.

FIG. 1A illustrates a garment 100 for comfortably securing one or more surgical drain evacuator pouches about a patient. Garment 100 includes a base panel 102, at least one expandable pouch 104, at least one flexible closure 106 for each expandable pouch 104, and adjustable belt 110. In embodiments, base panel 102 can be assembled from one or more parts which accommodate one or more expandable pouches 104 apiece to form garment 100. Base panel 102 includes an inward face that faces a patient wearing garment 100 and an outward face from which expandable pouch 104 expands. In embodiments, expandable pouch 104 can be structurally completed by base panel 102. In alternative embodiments, expandable pouch 104 includes front and back portions defining a pouch independent of base panel 102. While base panel 102 is shown in a substantially rectangular configuration, others can be utilized without departing from the scope or spirit of the innovation. The geometry of base panel 102 can completely back, partially back, or extend beyond the geometry of expandable pouch 104. In embodiments, base panel 102 can include rounded corners. An inside of base panel 102 can also include materials for the comfort or fit of a wearer, including but not limited to non-slip material, padding, wicking material, et cetera.

Expandable pouch 104 can be attached to an outward face of base panel 102. Each expandable pouch 104 is configured to receive a surgical drain evacuator. Expandable drain pouch 104 is not elastic or stretched, but deforms without imparting substantial inward pressure or otherwise being biased toward returning to a flattened or less voluminous configuration. In an embodiment, this expandable aspect can be accomplished using pleat 108. In embodiments, pleat 108 can be an inverted box pleat that allows expandable drain pouch 104 to expand outward and collapse back to a flattened (or flatter) configuration without the use of elastic or stretching materials. Additional pleats (including use of different pleat types as well as two or more pleats for a single expandable drain pouch 104), folds, gathers, or other arrangements for bunching or securing excess material can be used alone or in conjunction with one another as part of, or as alternative or complementary arrangements to, pleat 108. Pleats 108 may be sewn at a top (or other side or portion of expandable drain pouch 104) and re-sewn at another location and sewing can be completed on two or more sides of a pleat.

In embodiments, an amount of material for pleat 108 can be based on a difference between the unfilled and filled sizes (e.g., volume) of a surgical drain pouch, and an amount of material for expandable drain pouch 104 can be based on one or both of the filled and unfilled sizes of the surgical drain. In embodiments, multiple expandable drain pouches 104 of different sizes, or multiple pleats 108 of different sizes, can be used in a single garment 100 to accommodate multiple drain pouches which can be larger or smaller to accommodate drainage from one, two, or more incisions or drains. In alternative or complementary embodiments, multiple expandable drain pouches 104 of different sizes, or multiple pleats 108 of different sizes, can be used in a single garment 100 to accommodate multiple drain pouches which can be larger or smaller to provide balance, comfort, or other ergonomic effect (e.g., allow arms to move freely at sides by reducing thickness). In embodiments such as that shown, expandable drain pouches 104 and/or pleats 108 can be substantially symmetrical.

As noted above, expandable pouch 104 can be completely backed (e.g., at least one dimension of expandable pouch 104 matches a dimension of base panel 102), partially backed (e.g., at least one dimension of expandable pouch 104 is greater than a dimension of base panel 102), or over-backed (e.g., at least one dimension of expandable pouch 104 is less than a dimension of base panel 102) by base panel 102. The geometry of expandable pouch 104 may be different from that illustrated. Moreover, the geometry of expandable pouch 104 may deviate from that of base panel 102 (e.g., circular or triangular expandable pouch over rectangular base panel) or may be oriented differently (e.g., expandable pouch same shape as base panel but rotated).

Utilization of pleat 108 (or other configurations of cloth allowing the expansion of pouches formed of inelastic material) assists surgical drain applications by avoiding excess inward pressure on surgical drain pouches. Surgical drain evacuator pouches are typically provided in a flattened configuration. As surgical fluids are deposited into the surgical drain evacuator pouches via the surgical drain evacuators, the surgical drain evacuator pouches expand. This expansion should not be resisted or undone by anything containing or supporting the surgical drain evacuator pouch to ensure that drainage is facilitated and no back-flow of drained fluid occurs. If elastic materials were used, it is possible that the surgical drain evacuators might not open or establish suction, or it is possible that they may begin to back-flow depending on the forces from the stretched elastic materials and other external forces.

While pleat 108 (and other pleats herein) are shown oriented vertically with respect to the top of the pouch, it is understood that pleats oriented in other directions (e.g., horizontal, diagonal) can be utilized without departing from the scope or spirit of the disclosure.

Expandable pouch 104 has a corresponding flexible closure 106. The flexible closure 106 can be a flat or flattenable piece of cloth capable of being moved or rearranged to allow empty and/or full surgical drain evacuator pouches to be inserted into and removed from expandable pouch 104. In embodiments, one or more edges of a piece of cloth (or other material) comprising closure 106 can be attached along some or all of one or more edges of base panel 102 or expandable pouch 104. In embodiments, the orientation of portions of expandable pouch 104 to which closure 106 attach can resist opening of expandable pouch (e.g., because of tension placed on the attached portions of closure 106 by expandable pouch 104 when it is flattened with an empty surgical evacuator pouch therein, because of tension placed on the attached portions of closure 106 by expandable pouch 104 when weight from a full surgical drain evacuator pouch is stored therein). A piece of cloth or material comprising closure 106 can be triangular, semi-circular, or other shapes, and can align with the un-attached edges of the opening or hang freely within the opening or overlapping portions of expandable pouch 104. In alternative embodiments, flexible closure 106 can include a static or movable cinch, snap, hook and loop fastener set, eyelet, clasp, et cetera.

While flexible closures herein are often described or indicated at the top of a pouch, it is understood that flexible closures may be positioned different in all embodiments herein. For example, a flexible closure could be placed on the inside of base panel (or vest, hat, or other garment), on a side, at a corner of a pouch, et cetera, to best facilitate the garment's use.

Flexible closure 106 can be configured to allow a surgical drain evacuator to pass therethrough whether opened or closed, although the route of the surgical drain evacuator may change based on the positioning of flexible closure. In this regard, some or all of flexible closure 106 can remain open or unsecured in various configurations capable of securing a surgical drain evacuator in flexible pouch 104. In embodiments, flexible closure does not "open" or "close," but can be moved (thereby creating additional space to place items in or remove items from flexible pouch 104. Alternatively or complementarily, flexible closure 106 can close around a surgical drain evacuator (e.g., staggered buttons or hook and loop that closes about a tube), allowing it to pass through the closed expandable pouch 104. Moreover, while flexible closures can include only inelastic or loose material, alternative embodiments may utilize elastic material, cinches, or other closable or self-closing elements to further secure a surgical evacuator and allow fluid communication with associated drains without applying pressure to the evacuator.

Adjustable belt 110 can attach to base panel 102 on a first panel side. Attachment to the first panel side can be fixed by stitching, weaving, permanent adhesives, et cetera. Adjustable belt can be formed of multiple portions, including elastic portion 112 and fastening portion 114. Fastening portion 114 can removably attach to a second panel side. The inner face of the second panel side can be arranged to both secure fastening portion 114 and for wearer comfort. For example, a loop portion of a hook and loop arrangement can be arranged on an inner face of base panel 102 such that, if portions of the attachment faces are exposed, a softer portion faces the wearer of garment 100. A hook portion would correspondingly be on fastening portion 114 and face away from a wearer of garment 100. In embodiments, elastic portion 112 can comprise a center section of adjustable belt 110, flanked by inelastic portions to either side. In an alternative embodiment, elastic portion 112 can extend from the edge of base panel 102 until fastening portion 114. In embodiments, elastic portion 112 can extend from the edge of base panel 102 and can be separated from fastening portion 114 by an inelastic portion. In embodiments, elastic portion 112 can extend the entire length of adjustable belt 110, with fastening material for fastening portion 114 overlaid thereon. In embodiments, multiple elastic portions 112 can be separated by inelastic portions along the length of adjustable belt 110 (e.g., in alternating 1" sections, alternating 2" sections, et cetera). In some embodiments, elastic portion 112 can be used with a gather 113 in one or more locations (e.g., excess material corresponding to elastic portion 112 bunched in one or more locations along the length of adjustable belt 110). In embodiments, different portions of adjustable belt 110 can have different elasticities, with more, less, or different elastic material disposed at different portions to provide fit, stability, and/or comfort. While gather 113 is shown at the center of adjustable belt 110, it is understood that alternatives in the placement of gather 113 or a number of gathers along adjustable belt 110, such as those described above or as can be imagined by the designer, are embraced by the scope and spirit of this disclosure.

In embodiments, additional materials can be coated onto or interleaved in adjustable belt 110. For example, a comfort padding or material can be placed on portions of adjustable belt 110 (or the inner face of base panel 102). Alternatively, a friction-increasing material (e.g., rubber) can be applied to at least a portion of adjustable belt and/or the inner face of base panel 102 to prevent slipping by garment 100 when worn.

While adjustable belt 110 as shown is adjustable based on the attachment of fastening portion 114 to an inside of base panel 102 and/or stretching of elastic portion 112, alternative or complementary arrangements can be utilized without departing from the scope or spirit of the innovation. Buckles, clamps, snaps, rings or double-rings, auto-grips or auto-locks, clasps, clips, pins, flap closures, latches, and other arrangements for adjustably securing a belt or strap can be utilized with garment 100 and other garments herein without departing from the scope or spirit of the disclosure.

In embodiments, an inside of adjustable belt 110 can also include materials for the comfort or fit of a wearer, including but not limited to non-slip material, padding, wicking material, et cetera.

Figure 1B:
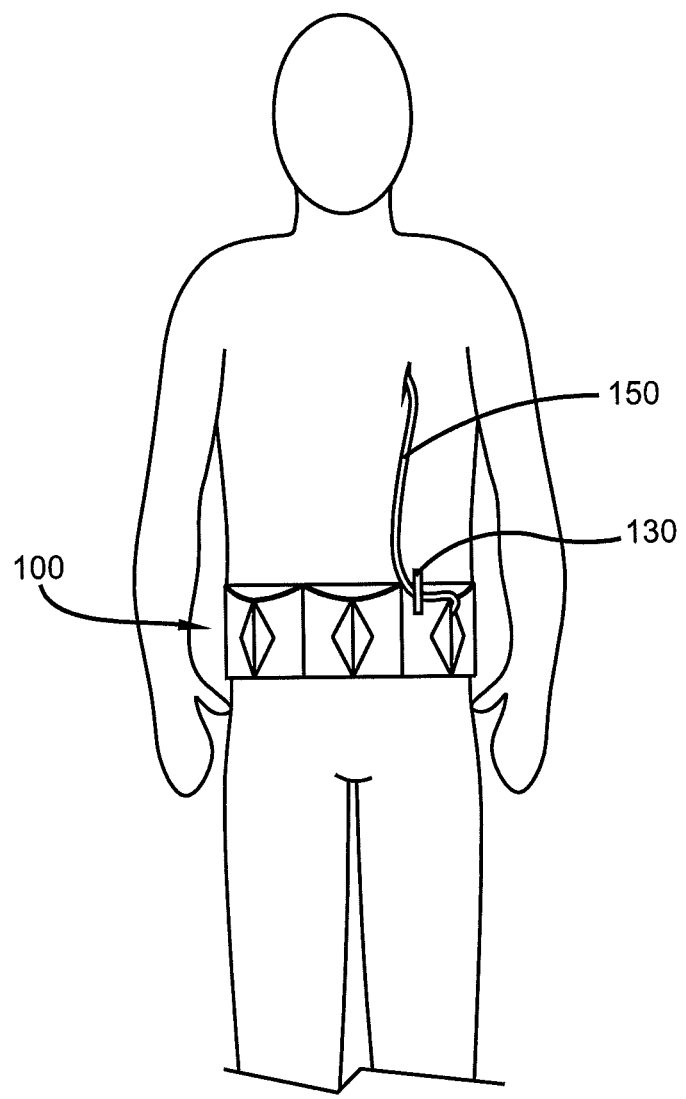
FIG. 1B illustrates an example embodiment of a drain supporting apparatus worn by a user as disclosed herein.

FIG. 1B illustrates an example embodiment of garment 100 as worn by a user. Surgical drain 150 extends from an incision to drain fluid to one or more surgical drain evacuators within garment 100. Garment 100 can include a safety mechanism 130 for reducing risk to the incision site, surgical drain 150, or evacuator. For example, safety mechanism 130 can hook, clip, or retain surgical drain 150 in a manner that slack is provided on one or both ends to allow motion without pulling at an incision or evacuator. Alternatively or complementarily, safety mechanism 130 can retain surgical drain 150 closer to the body to decrease the likelihood it is snagged, and also allow wear to be more discreet.

FIG. 2 illustrates an alternative garment 200 for comfortably securing one or more surgical drain evacuator pouches about a patient. Garment 200 is shown with two straps, 210 and 210', and one expandable pouch 204, but may have greater or fewer straps and/or pouches without departing from the scope or spirit of the disclosure.

Expandable pouch 204 is formed with pleat 208 and/or other arrangements of material allowing pouch 204 to expand outward from base panel 202. Flexible closure 206 is configured to allow surgical drain pouches to pass therethrough for storage in pouch 204, and in embodiments permits a surgical drain to pass through when a surgical drain pouch is installed in pouch 204.

Straps 210 and 210' can be attached to base panel 202. In embodiments, straps 210 and 210' can include hook portion 214 and loop portion 216 to secure the straps in loops of varying sizes about appendages of a wearer. In alternative embodiments, other techniques can be used for sizing, including but not limited to buckles, buttons or snaps, and closed-loop straps utilizing custom sizing or stretchable materials. Straps 210 and 210', like other straps or belts herein, can be configured to resist movement or slipping by way of coatings or impregnated materials.

Figure 2A:
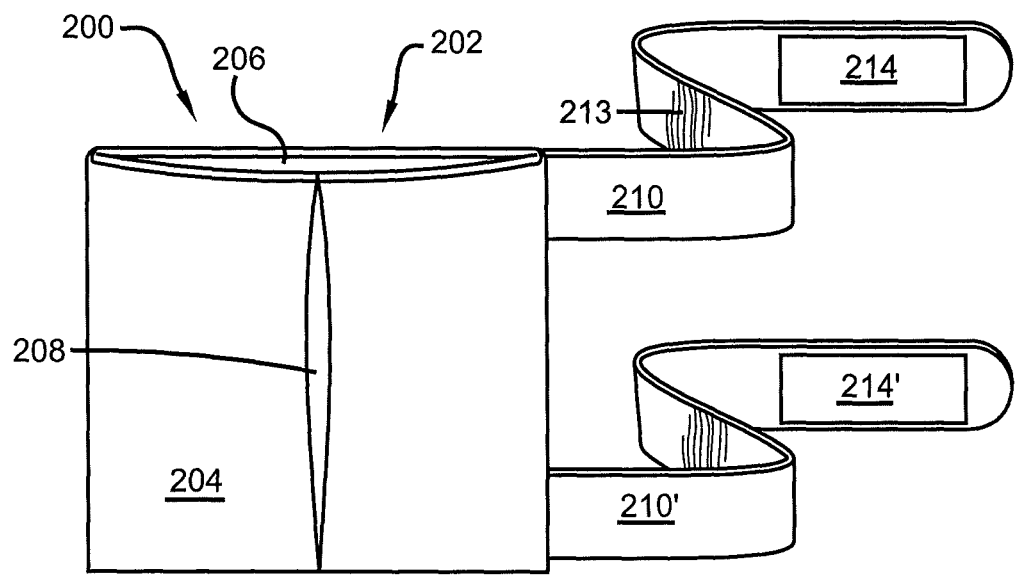
FIG. 2A, FIG. 2B, FIGS. 2C, and 2D illustrate example embodiments of a drain supporting apparatuses disclosed herein.
Figure 2B:
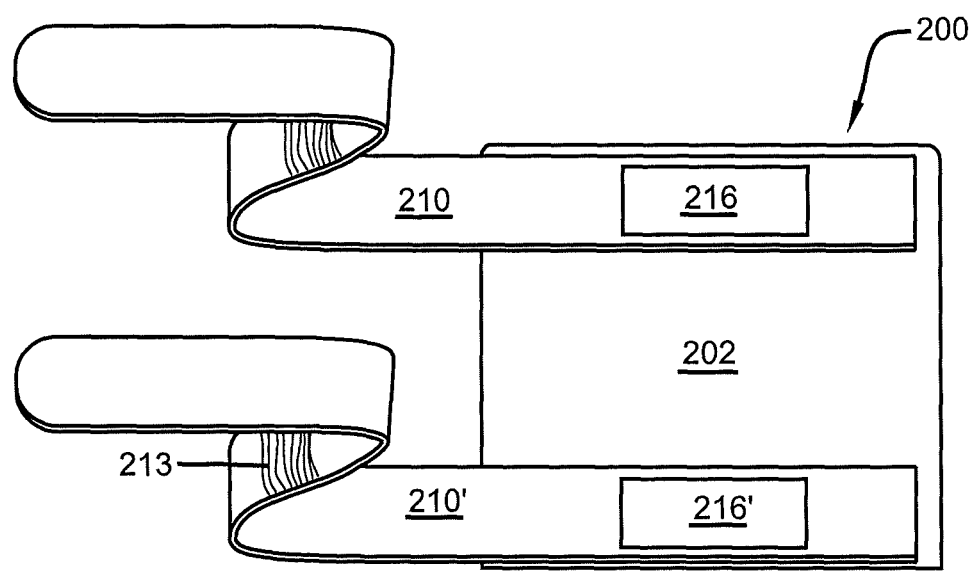
Figure 2C:
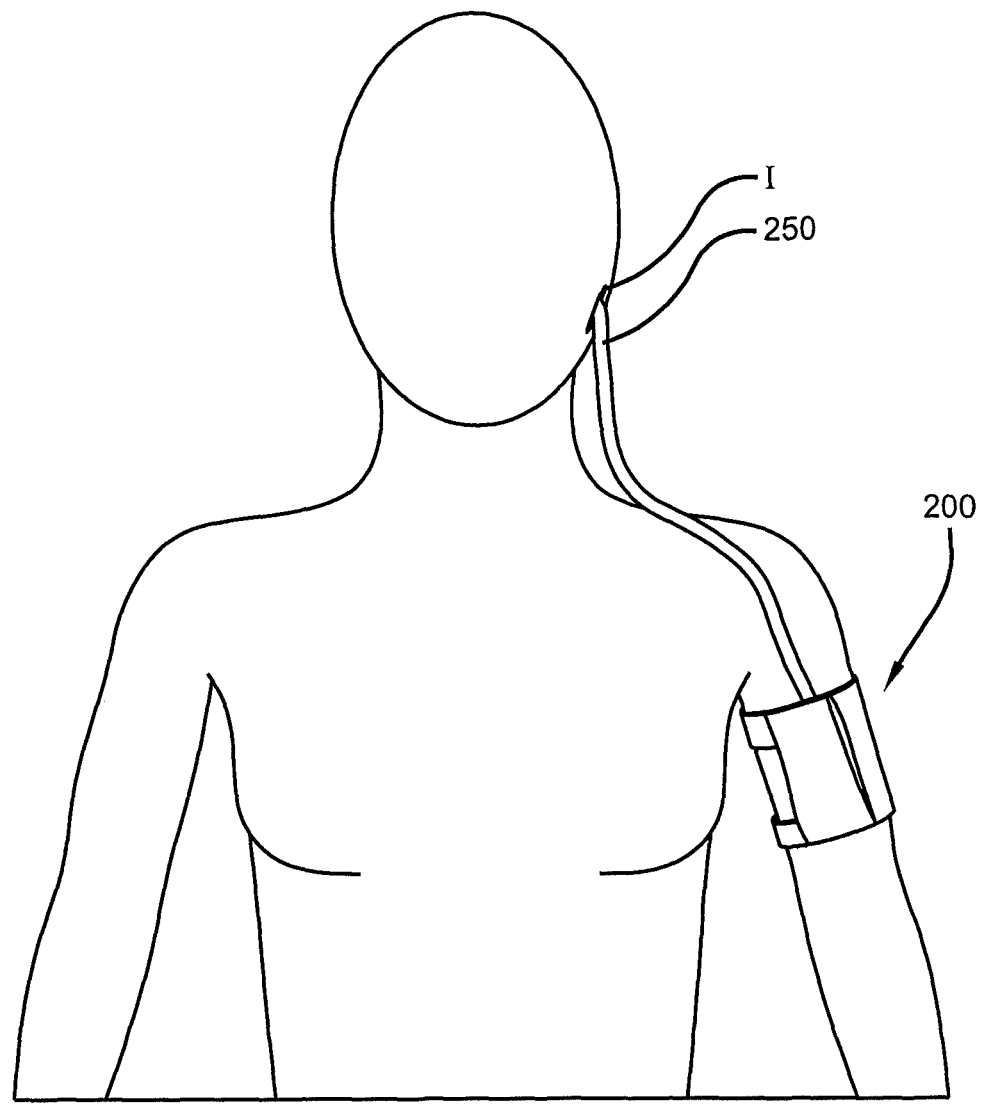
Figure 2D:
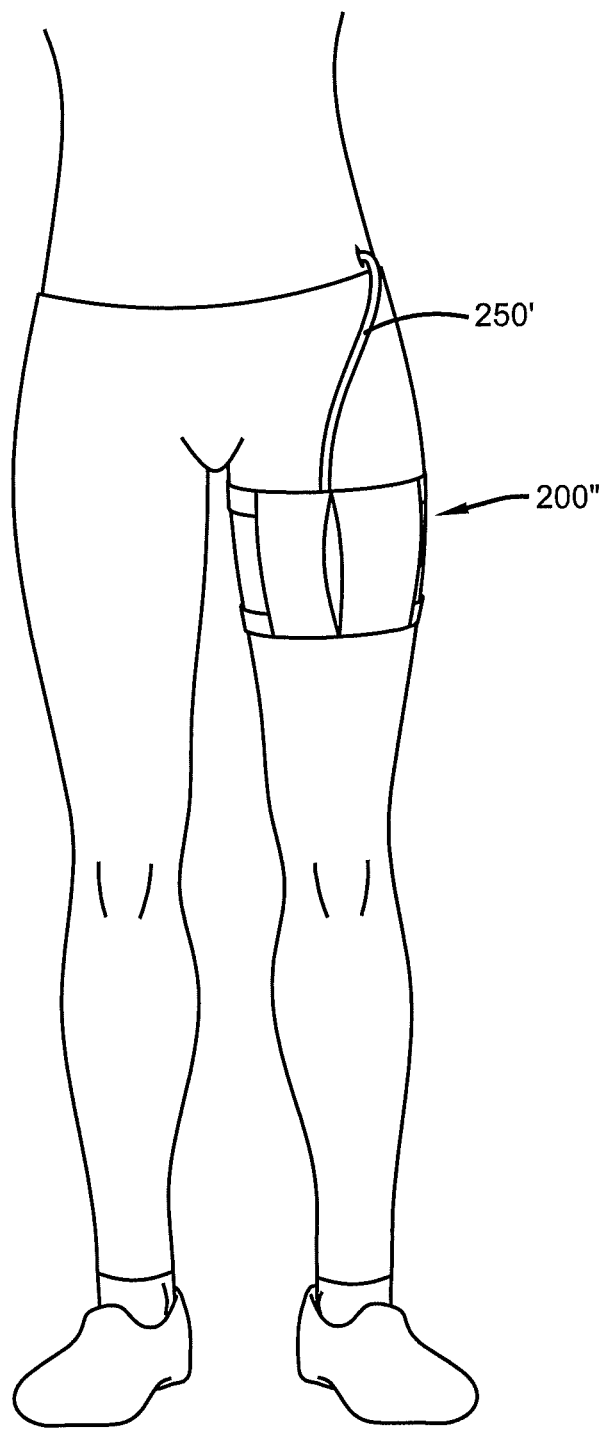

FIG. 2C illustrates an example embodiment of use of garment 200' in which surgical drain 250 travels from incision I to garment 200' containing a surgical drain pouch to collect drained fluid. Garment 200' is attached about the wearer's upper arm, permitting proximity to the site of incision I in the head or neck. Similarly, FIG. 2D illustrates an example embodiment of use of garment 200" in which surgical drain 250' travels from incision I' to garment 200" containing a surgical drain pouch to collect drained fluid. Garment 200" is attached about the wearer's upper leg, permitting proximity to the site of incision I' in the torso. As can be understood, the flexibility of disclosed garments 200/200'/200" allows for improved safety and drainage by reducing the length of a surgical drain used in conjunction therewith in comparison with surgical drains positioned at locations more distant from the incision.

In embodiments, the garments of FIG. 2A, FIG. 2B, FIG. 2C, and/or FIG. 2D may be arranged to prevent slippage. As these garments may be arranged about at thicker or higher portion of an arm (e.g., bicep in comparison to forearm) or leg (e.g., quadricep in comparison to knee or calf), they may be prone to slipping. As such, slip-resistant material can be applied to the inside of straps as described herein. Moreover, other accessories may be utilized, such as an inelastic or elastic strap connecting a leg garment to a belt or an arm garment to a shoulder or torso. With such accessories, an anchor point can be provided to prevent substantial movement of a garment from the position at which it was attached. Such accessories may be removable or adjustable to don, doff, and adjust to the proper length for anchoring the garment to prevent movement or to allow only natural movement without significant slipping. Inside-facing surfaces of these garments can also include materials for the comfort or fit of a wearer, including but not limited to non-slip material, padding, wicking material, et cetera. Straps in this and other embodiments or garments may also include gather 213 around elastic portions to bunch material which can be stretched or extended. In embodiments, gather 213 or other material can be included on one or more of two or more straps 210 and 210'. For garment 200 and other garments including two or more straps, the straps can be substantially identical, or formed of different construction in size, shape, or material. For example, an upper strap can be larger or more flexible to accommodate a larger portion of the arm or leg, or straps could be arranged with differing elasticity or slip-resistant materials to more fixedly position the garment.

In embodiments, garment 200 can include only one strap 210, which can be centered, arranged along an edge of expandable pouch 204, or offset from the center or edge. For example, strap 210 may be operatively coupled with expandable pouch 204 above its center or below its top edge to allow expandable pouch 204 to hang therefrom. In an embodiment, two straps, 210 and 210', can be arranged in a mirrored fashion along two or more axes (e.g., both along opposite edges, both offset from center or opposite edges by an equal amount) or may be arranged in asymmetrical orientations (e.g., a first strap arranged along an edge and a second strap rotated out of parallel with the first, offset different amounts from edge or center, offset different amounts from a third or next strap).

Figures 3A, 3B:
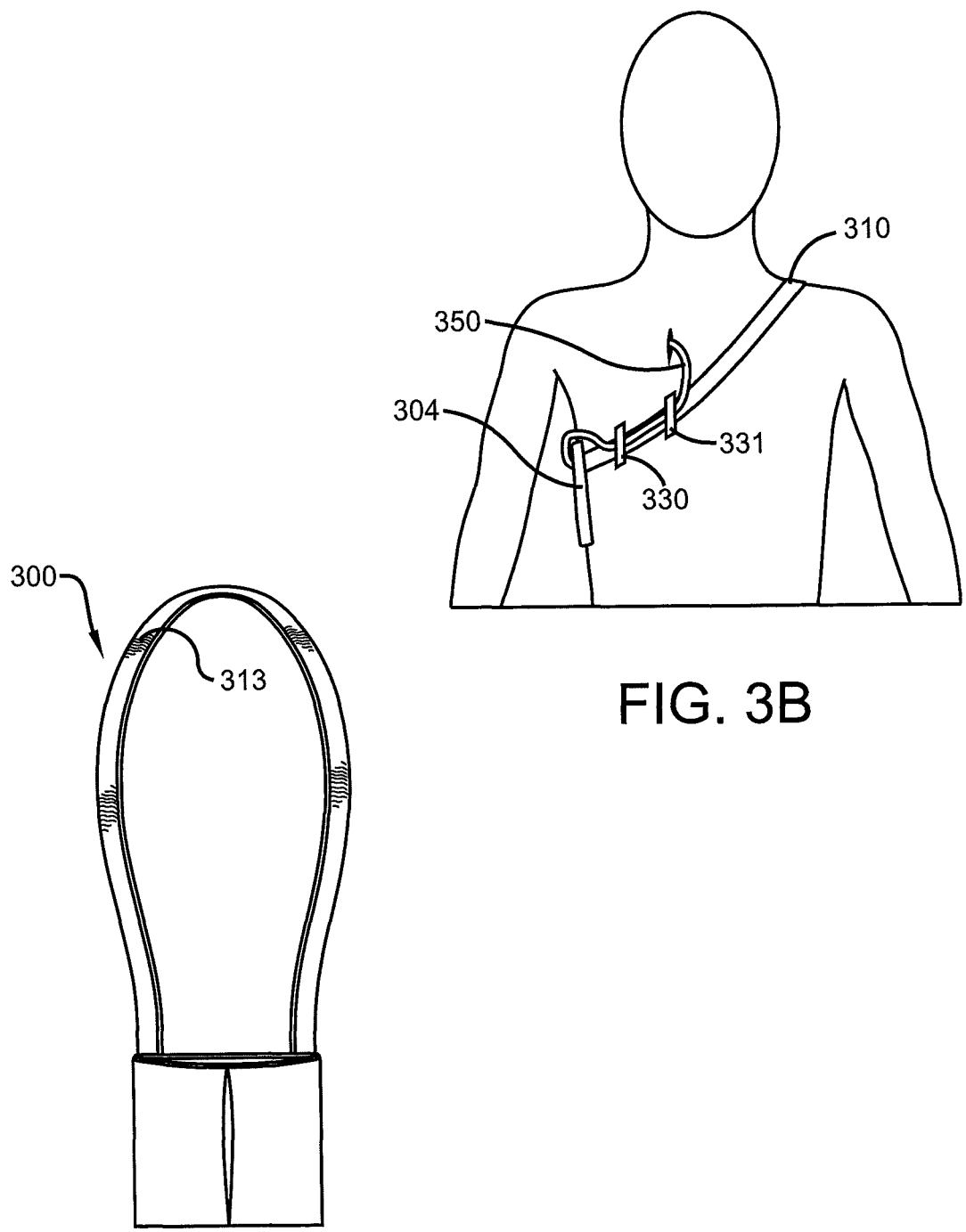
FIG. 3A and FIG. 3B illustrate another example embodiment of a drain supporting apparatus disclosed herein.

FIG. 3A and FIG. 3B illustrate an over-the-shoulder variant garment 300 that can be worn outside or beneath closing. Garment 300 can include one or more expandable pouches 304 with a flexible closure configured to accept surgical drains and surgical drain pouches. The expandable pouches can include one or more pleats and may be shaped to minimize impact on wearer's range of motion with the arm over top of the expandable pouch 304.

Garment 300 is held in place on a wearer by one or more straps 310 that can be fixed or adjustable in length and elastic or inelastic. Where a strap 310 is elastic, a gather 313 can be included in one or more locations or along some or all of the length. In embodiments, a cross-chest or cross-belly strap can be provided to complement the over-the-shoulder strap 310 to further stabilize or anchor a surgical drain and/or surgical drain pouch. Garment 300 can be configurable to be positioned at different heights or positions along a wearer's body, and can be rotated to the front, rear, or either side to place garment 300 in proximity to an incision and/or a position maximizing comfort or freedom of motion.

Expandable pouch 304 can be attached to strap 310 in varying configurations. In embodiments, an edge of expandable pouch 304 can be aligned with an edge of strap 310. In alternative embodiments, such edge attachments can be angled or oriented in a manner that allows expandable pouch 304 to hang or rest at a particular angle. Strap 310 can be attached to a top, bottom, center, or side of expandable pouch 304 to provide a desired orientation, support, et cetera. Inside-facing surfaces of garment 300 can also include materials for the comfort or fit of a wearer, including but not limited to non-slip material, padding, wicking material, et cetera.

Garment 300 can include one or more safety mechanisms 330, 331, et cetera, to secure surgical drain 350. Safety mechanism 330 (and any others such as safety mechanism 331) can reduce risk to the incision site, surgical drain 350, or evacuator. For example, safety mechanisms 330, 331, et cetera can hook, clip, or retain surgical drain 350 in a manner that slack is provided on one or both ends to allow motion without pulling at an incision or evacuator. Alternatively or complementarily, safety mechanisms 330, 331, et cetera can retain surgical drain 350 closer to the body to decrease the likelihood it is snagged, and also allow wear to be more discreet. Any number of safety mechanisms, from zero to any in the designer's imagination, can be included in garments disclosed herein. Moreover, safety mechanisms need not provide a safety feature at a discrete point, but can run some or all of the length of garment elements with which they interact. For example, strap 310 can include one or more closures (i.e., lengths of hook and loop material, material with snaps or zipper on edges, et cetera) running some or all of the length of strap 310 which can retain equal or greater lengths of surgical drain 350, shielding surgical drain 350 and preventing separation of surgical drain 350 from strap 310 along those lengths unless the closure is opened.

Figure 4A:
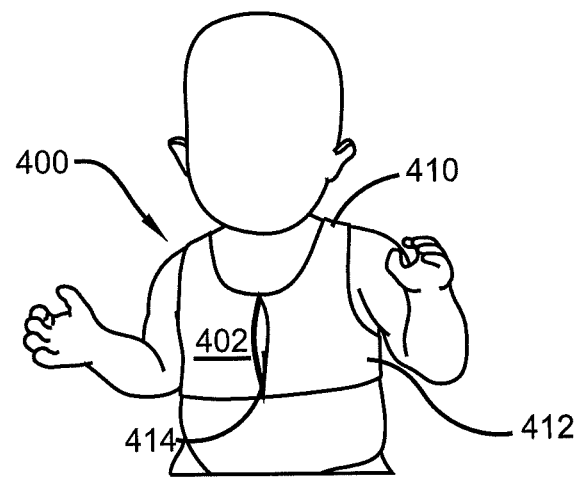
FIG. 4A and FIG. 4B illustrate another example embodiment of a drain supporting apparatus disclosed herein.
Figure 4B:
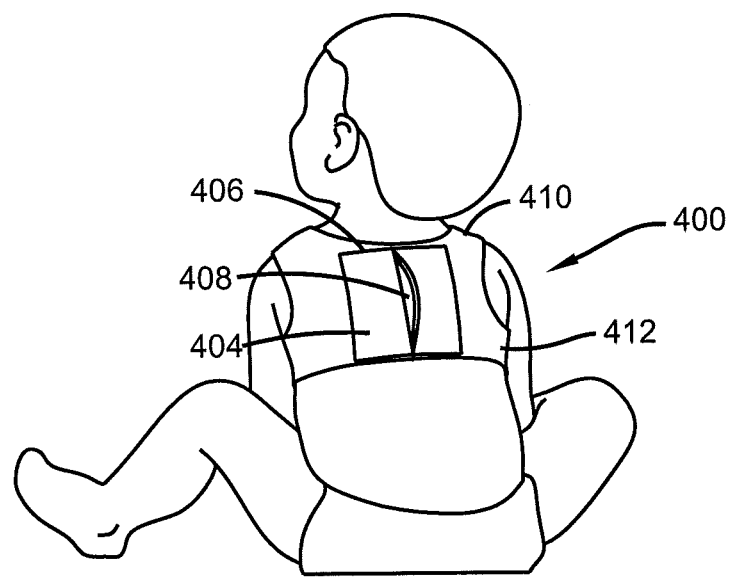

FIG. 4A and FIG. 4B illustrate vest-style garment 400, shown in conjunction with a pediatric patient, but that may be used with patients of any size or age. Garment 400 includes base 402, expandable pouch 404 with flexible closure 406 and pleat 408. Shoulder straps 410 and torso strap 412, which can be portions of base 402, secure garment 400 about the wearer. Base 402 can be formed in part or whole of elastic materials, or be formed of inelastic materials. An inside of base 402 can also include materials for the comfort or fit of a wearer, including but not limited to non-slip material, padding, wicking material, et cetera.

Garment 400 can include vest closure 414. Vest closure 414 can comprise, e.g., zippers, buttons, snaps, hook and loop, et cetera, and be user-friendly (e.g., for adult patients) or child-resistant (e.g., for pediatric patients). Vest closure 414 can allow adjustment to the garment 400 by fitting to a chest measurement of a wearer, or alternatively may be designed in a one-size-fits-all arrangement. In embodiments, vest closure 414 can be located in other locations than the center of the chest (e.g., at back). In alternative embodiments, a vest can exclude any vest closure, and instead be pulled over a wearer's arms and head. In still further embodiments, one or more of shoulder straps 410 and torso strap 412 includes a removable end to allow for donning and doffing of garment 400.

Figure 5A:
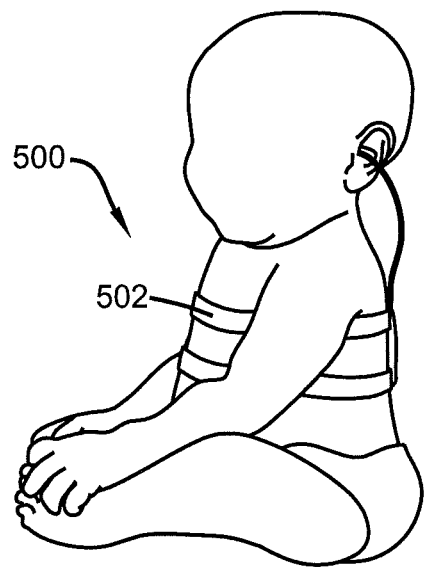
FIG. 5A and FIG. 5B illustrate another example embodiment of a drain supporting apparatus disclosed herein.
Figure 5B:
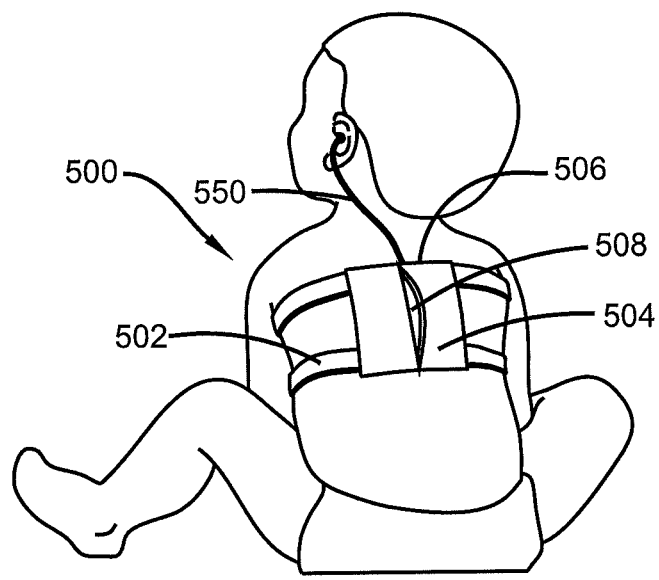

FIG. 5A and FIG. 5B illustrate a "strapless" vest-style garment 500 based on the lack of straps going over the wearer's shoulders. As with the preceding figures, garment 500 is shown in conjunction with a pediatric patient, but that may be used with patients of any size or age.

Garment 500 includes one or more straps 502, which can be affixed in a loop configuration or detachable on one or both ends for donning and doffing garment 500. Straps 502 can include slip-resistant material in embodiments. Straps 502 can be of different lengths, or attached or tightened to different tensions, to ensure that garment 500 does not move when donned. In embodiments, some or all of straps 502 and/or expandable pouch 504 or a base panel connected thereto can be formed of elastic.

Surgical drain 550 (or other drain) can be fed into expandable pouch 504 through flexible closure 506 to receive fluid drainage. Pleat 508 allows expandable pouch 504 to expand or flatten depending on the amount of fluid in a surgical drain pouch placed in expandable pouch 504. In alternative embodiments expandable pouch 504 can be attached asymmetrically to one or more straps to allow expandable pouch 504 to hang or orient in a particular manner when empty or full. Inside-facing surfaces of garment 500 can also include materials for the comfort or fit of a wearer, including but not limited to non-slip material, padding, wicking material, et cetera.

In FIG. 4A, FIG. 4B, FIG. 5A, and FIG. 5B the location of garment 400 or 500 can be convenient for an incision, but may also prevent a pediatric patient from interfering with drainage by placing the expandable pouch(es), as well as associated surgical drain equipment and drained fluid, outside the wearer's reach. Further, as with other figures, embodiments embraced under the disclosures of FIG. 4A, FIG. 4B, FIG. 5A, and FIG. 5B can vary in the number of expandable pouches, straps, or other components.

Figure 6A:
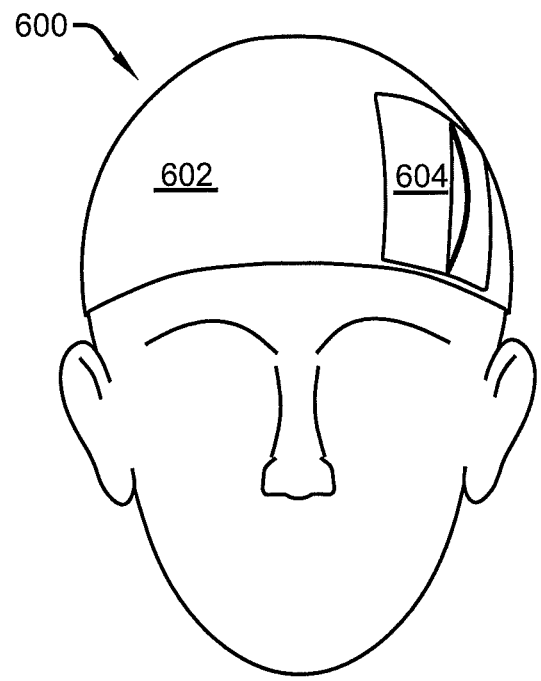
FIG. 6A, FIG. 6B, and FIG. 6C illustrate another example embodiment of a drain supporting apparatus disclosed herein.
Figure 6B:
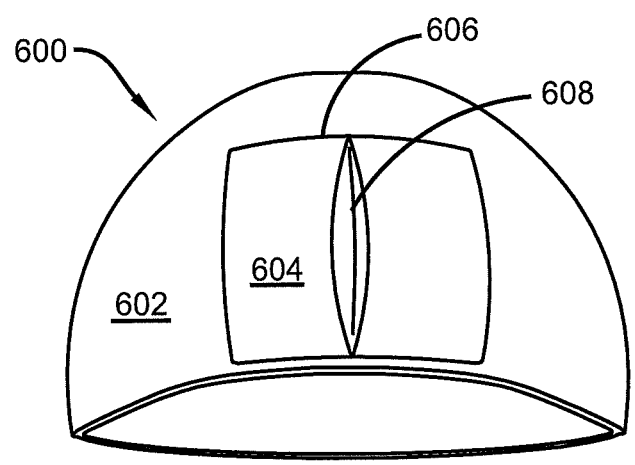
Figure 6C:
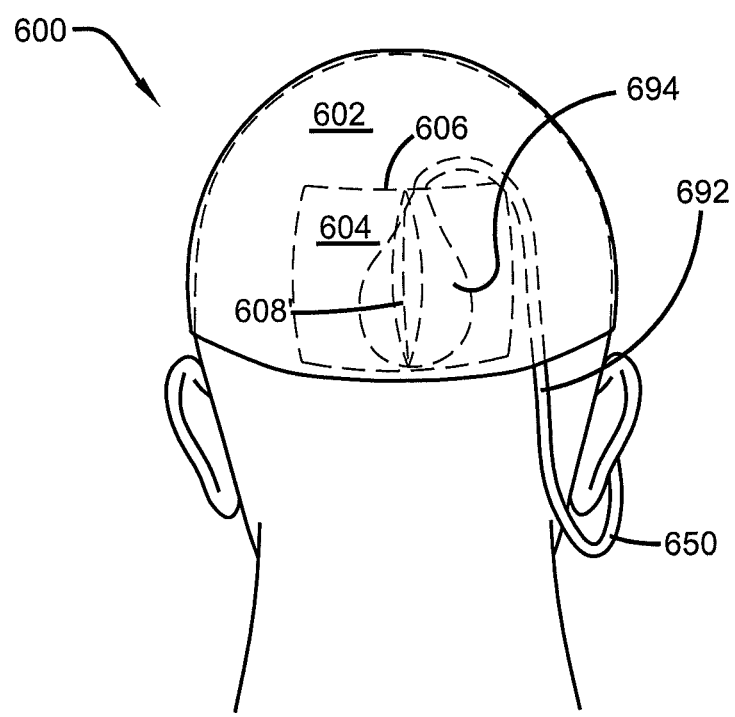

Turning to FIG. 6A, FIG. 6B, and FIG. 6C, illustrated is a head garment or cap 600 configured to hold a surgical drain pouch. Cap 600 includes cap 602 and expandable pouch 604. Cap 602 can be various sizes for different wearer head sizes, be formed of elastic materials to accommodate multiple sizes, or be one-size fits all with various means for changing the size (e.g., closures between flexible pieces which can be expanded or collapsed).

Expandable pouch 604 can include flexible closure 606 (which can be located outside or inside cap 602) with pleat 608. In embodiments, flexible pouch can have more than one flexible closure 606 to allow an evacuator tube to pass through a top, bottom, front, back, side, et cetera of expandable pouch 604. In embodiments, the surgical evacuator may be kept at least in part within cap 602 for both security of the evacuator and discreetness of the tubing. FIG. 6C illustrates cap 602 being worn in a different position than in FIG. 6A, and includes surgical drain 650 proceeding from a wearer's ear or other incision in the head. A surgical drain pouch is shown in broken lines within expandable pouch 604.

In embodiments, cap 600 can include two or more expandable pouches 604. This can permit additional drainage capacity and/or assist with balance and wear of cap 600. Inside-facing surfaces of cap 600 can include materials for the comfort or fit of a wearer, including but not limited to non-slip material, padding, wicking material, et cetera.

In garments for managing surgical drain pouches, various techniques can be utilized to maintain the safety of the surgical drain. While the drain can be sutured at the incision site or elsewhere, such sutures or tissue to which they are attached may be damaged if a line or tube is manipulated excessively. Lines or tubes extending between the incision or drainage site and surgical drain pouch can be secured in various manners, either on portions of garments disclosed herein or according to other techniques. In embodiments, garments herein can include loops or catches to maintain slack in a line, reducing the likelihood that the line is detached if snagged. In alternative or complementary embodiments, some or all of the line can run beneath a layer of material, or be held in place at its ends or along some or all of its length by hook and loop materials, adhesive materials, snaps, buckles, et cetera.

While the figures include common features for ease of description and illustration, it is understood that variants can be pursued without departing from the scope or spirit of the innovation. Portions of apparatuses can be shaped or sized differently in accordance with the imagination of the designer and/or to provide increase comfort, functionality, et cetera.

Figure 7:
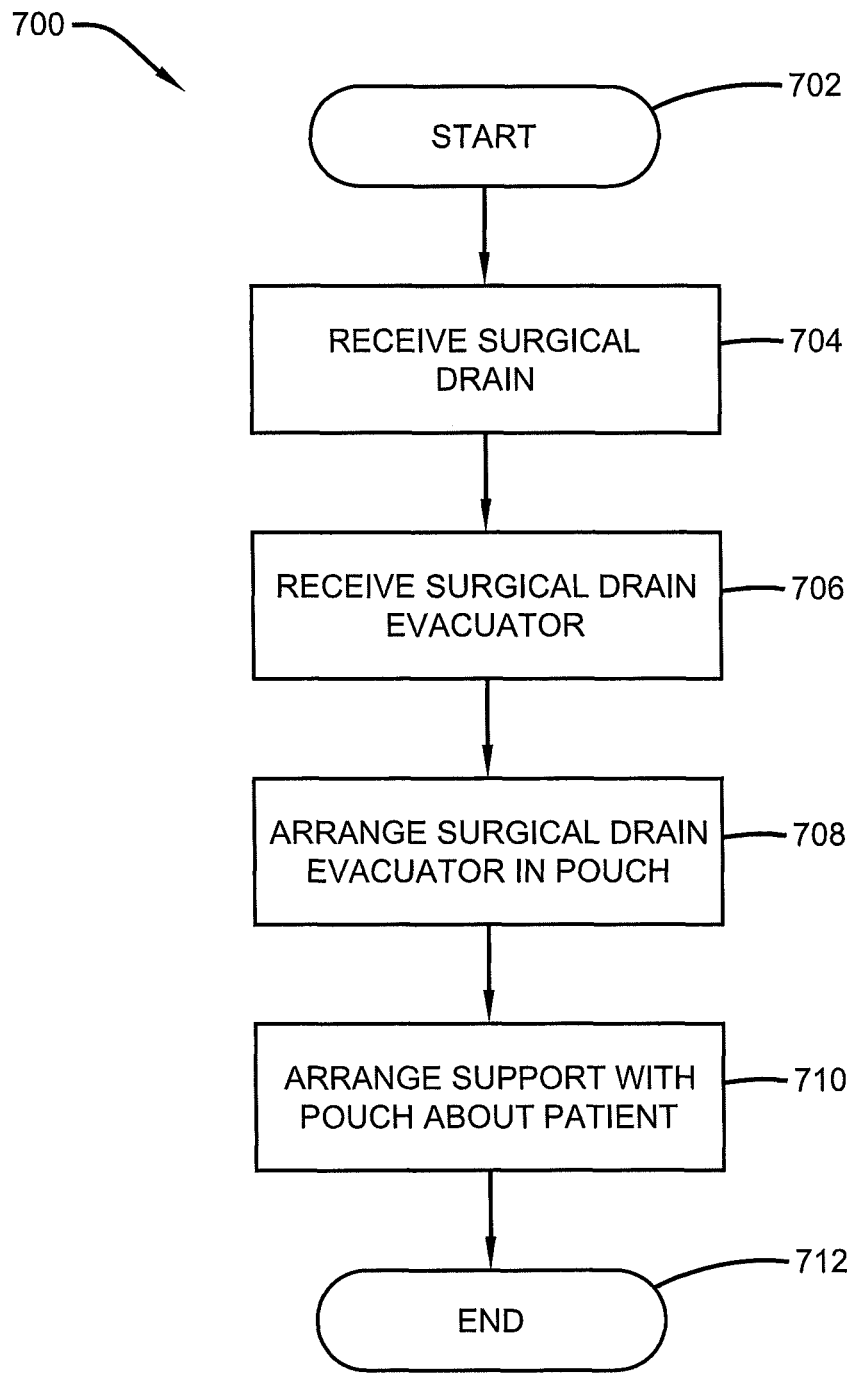
FIG. 7 illustrates an example methodology disclosed herein.

Turning to FIG. 7, illustrated is an example methodology 700 for arranging a surgical drain pouch about a patient. Methodology 700 begins at 702 and proceeds to 704 where a surgical drain is received. A surgical drain evacuator attached to the drain is received at 706 to store fluids received through the surgical drain. At 708, the surgical drain evacuator is arranged in an expandable pouch of a support garment for surgical drains and surgical drain evacuators. Thereafter, at 710, the support garment bearing the pouch can be arranged about the patient. Depending on the circumstance, the garment may be arranged around the patient before the surgical drain evacuator is arranged in the expandable pouch of the garment. Moreover, the garment may include more than one expandable pouch and other elements. In embodiments, surgical drain safety components may be included in the garment to avoid snagging or tugging on one or both ends of a surgical drain tube. A surgical drain pouch and/or support garment utilized in methodology 700 can be any described herein, combinations of embodiments described herein, and/or those within the scope of the disclosure.

Figure 8:
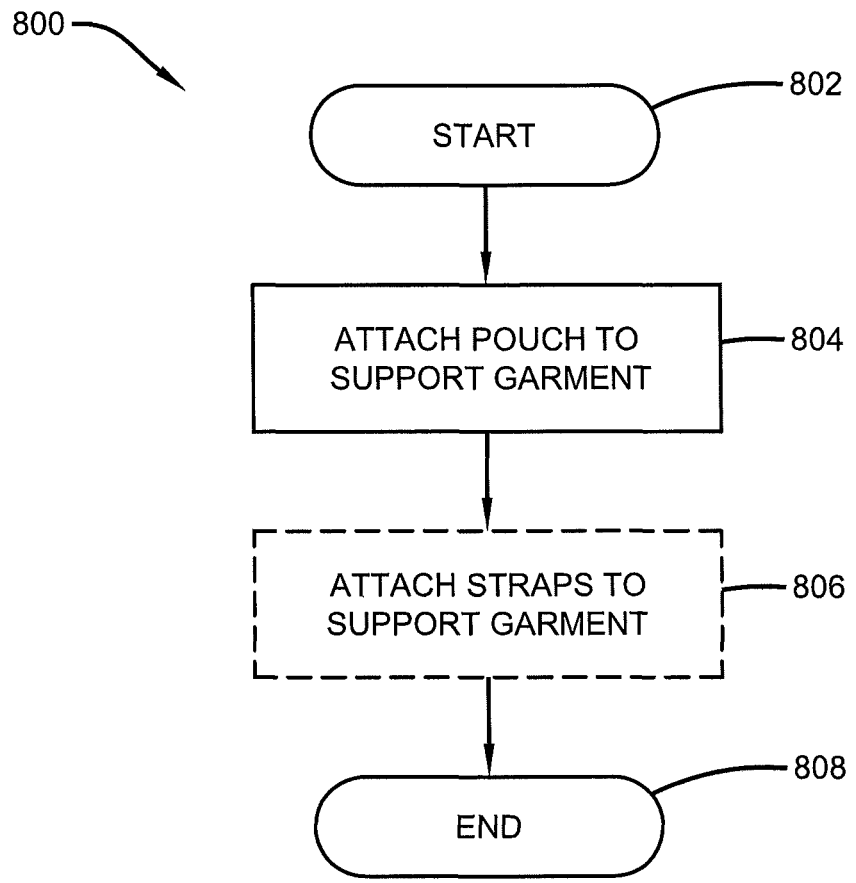
FIG. 8 illustrates another example methodology disclosed herein.

Turning to FIG. 8, illustrated is an example methodology 800 for attaching a surgical drain pouch to a support garment. Methodology 800 begins at 802 and proceeds to 804 where a pouch can be attached to, placed into, or otherwise arranged using a support garment. In embodiments where the pouch can be placed into the garment before it is worn, at 804 straps can be attached to the support garment to arrange it around the wearer. Once arranged, methodology 800 can end at 808. A surgical drain pouch and/or support garment utilized in methodology 800 can be any described herein, combinations of embodiments described herein, and/or those within the scope of the disclosure.

While aspects of the present disclosure have been particularly shown and described with reference to the examples above, it will be understood by those skilled in the art that various combinations of the disclosed aspects or additional aspects may be contemplated by the modification of the disclosed machines, systems and methods without departing from the spirit and scope of what is disclosed. Such aspects should be understood to fall within the scope of the present disclosure as determined based upon the claims and any equivalents thereof.

What is claimed is:

1. An apparatus for securing surgical drains and surgical drain evacuators about a patient, comprising:
   a base panel having a first panel side, a second panel side, an inward face, and an outward face;
   an expandable pouch fixedly attached to the outward face of the base panel and configured to receive a surgical drain evacuator through an open edge, wherein the open edge is disposed toward a panel top edge, and wherein a front side of the expandable pouch is formed of a flexible inelastic material fixedly attached to the base panel around a whole perimeter of the expandable pouch except the open edge, and wherein a back side of the expandable pouch is a portion of the base panel;
   a flexible closure of the expandable pouch formed of a flat piece of cloth fixedly attached at the top corners of the expandable pouch and configured to completely occlude the open edge of the expandable pouch, wherein the flexible closure permits fluid communication between the surgical drain evacuator and a surgical drain disposed at least in part outside the expandable pouch, wherein the flexible closure overlays all of the open edge of the expandable pouch, and wherein the flexible closure can be repositioned to access an inside of the expandable pouch; and
   an adjustable belt fixedly attached by sewing to the first panel side using a first belt end and configured to removably attach to the second panel side using a second belt end, wherein the adjustable belt is formed in part of an elastic material; and
   a gather of the adjustable belt, wherein the gather is disposed toward the center of the adjustable belt between two substantially inelastic sections.

2. The apparatus of claim 1, wherein the expandable pouch includes an inverted box pleat formed of flexible material.

3. The apparatus of claim 1,
   wherein the adjustable belt includes a hook portion on an outer surface and disposed toward the second belt end, and
   wherein the second panel side includes a loop portion on the inward face, wherein the loop portion is configured to mate with the hook portion.

4. The apparatus of claim 3, wherein the loop portion overlays all of the inward face.

5. The apparatus of claim 1, further comprising:
   the surgical drain; and
   the surgical drain evacuator.

6. The apparatus of claim 1, wherein a belt top edge is aligned to the panel top edge.

7. The apparatus of claim 1, comprising a second expandable pouch, wherein a first side edge of the expandable pouch aligns against a second side edge of the second expandable pouch.

8. The apparatus of claim 1, wherein one of the base panel and adjustable belt include a non-sensitizing material.

9. A garment, comprising:
   an expandable pouch configured to receive a surgical drain evacuator, wherein the expandable pouch is formed of a flexible inelastic material, and wherein the expandable pouch is formed at least in part by fixed attachment to a portion of a base panel around an entire perimeter of the expandable pouch except an opening;
   a flexible closure of the expandable pouch formed of a flat piece of cloth fixedly attached at the top corners of the expandable pouch and configured to completely occlude an opening of the expandable pouch, wherein the flexible closure permits fluid communication between the surgical drain evacuator and a surgical drain disposed at least in part outside the expandable pouch, wherein the flexible closure overlays all of the opening of the expandable pouch, and wherein the flexible closure can be repositioned to access an inside of the expandable pouch;
   a strap operatively coupled to the expandable pouch, wherein the strap is configured to attach about an anatomy of a wearer to whom the surgical drain is applied, wherein the strap is formed in part of an elastic material; and
   a gather of the strap, wherein the gather is disposed toward the center of the strap between two substantially inelastic sections.

10. The garment of claim 9, further comprising:
    second strap operatively coupled to the expandable pouch.

11. The garment of claim 9, further comprising:
    a detachable fastener coupled with one or more of the strap and the expandable pouch, wherein the detachable fastener secures the strap and the expandable pouch about the anatomy of the wearer when attached.

12. The garment of claim 9, wherein the expandable pouch includes an inverted box pleat formed of flexible material.

13. The garment of claim 9, wherein the strap includes a slip-preventing material on a portion of an inner surface, wherein the slip preventing material includes rubber to increase friction between the strap and a wearer.

14. The garment of claim 9, further comprising:
    a safety mechanism for the surgical drain, wherein the safety mechanism is one of a hook or a clip configured to provide slack between the safety mechanism and an incision in fluid communication with the surgical drain.

15. The garment of claim 9, wherein at least a portion of the garment includes a non-sensitizing material.

16. A method, comprising:
    providing a garment, wherein the garment includes:
       an expandable pouch configured to receive a surgical drain evacuator through an open edge, wherein the open edge is disposed toward a panel top edge, and wherein the expandable pouch is formed of a flexible inelastic material fixedly attached around the expandable pouch's entire perimeter to a base panel except the open edge, and wherein a back side of the expandable pouch is a portion of the base panel, a flexible closure of the expandable pouch formed of a flat piece of cloth fixedly attached at the top corners of the expandable pouch and configured to completely occlude the open edge of the expandable pouch when closed, wherein the flexible closure permits fluid communication between the surgical drain evacuator and a surgical drain disposed at least in part outside the expandable pouch, and wherein the flexible closure overlays all of the open edge of the expandable pouch, and wherein the flexible closure can be repositioned to access an inside of the expandable pouch, a strap operatively coupled to the expandable pouch, wherein the strap is configured to attach about anatomy of a wearer to whom the surgical drain is applied, wherein the strap is formed in part of an elastic material, and a gather of the strap, wherein the gather is disposed toward the center of the strap between two substantially inelastic sections; and passing the surgical drain evacuator through the flexible closure to arrange the surgical drain evacuator in the expandable pouch, wherein the surgical drain passes through the flexible closure to a drainage site.

17. The method of claim 16, further comprising:
arranging the strap around anatomy of a user, wherein the drainage site is on the user, and
arranging a second strap around anatomy of the user, wherein the garment includes the second strap.

18. The method of claim 16, further comprising:
securing the surgical drain using a safety mechanism, wherein the safety mechanism is one of a hook or clip, and wherein the safety mechanism is configured to provide slack between the safety mechanism and an incision in fluid communication with the surgical drain.

19. The method of claim 16, wherein the garment includes a non-sensitizing material.

* * * * *